US00PP30970P2

(12) United States Plant Patent
Clark

(10) Patent No.: US PP30,970 P2
(45) Date of Patent: Oct. 22, 2019

(54) ***COLEUS* PLANT NAMED 'UF15-6-28'**

(50) Latin Name: *Plectranthus scutellarioides*
Varietal Denomination: UF15-6-28

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/350,116

(22) Filed: Sep. 26, 2018

(51) Int. Cl.
*A01H 5/00* (2018.01)
*A01H 6/50* (2018.01)

(52) U.S. Cl.
USPC ..... Plt./373

(58) Field of Classification Search
USPC ..... Plt./373
CPC ..... A01H 5/00; A01H 6/50
See application file for complete search history.

(56) References Cited

U.S. PATENT DOCUMENTS

PP28,566 P2 10/2017 Clark

OTHER PUBLICATIONS

U.S. Appl. No. 15/732,774, filed Dec. 27, 2017, Clark.
U.S. Appl. No. 15/732,779, filed Dec. 27, 2017, Clark.
U.S. Appl. No. 15/732,777, filed Dec. 27, 2017, Clark.
U.S. Appl. No. 15/732,776, filed Dec. 27, 2017, Clark.
U.S. Appl. No. 15/732,778, filed Dec. 27, 2017, Clark.
U.S. Appl. No. 16/350,114, filed Sep. 26, 2018, Clark.
U.S. Appl. No. 16/350,113, filed Sep. 26, 2018, Clark.
U.S. Appl. No. 15/732,775. filed Dec. 27, 2017, Clark.
Variety specific information as indicated in transmittal letter Information Disclosure Statement for U.S. Appl. No. 16/350,116, filed Mar. 26, 2019.

*Primary Examiner* — Annette H Para
(74) *Attorney, Agent, or Firm* — Dentons US LLP

(57) ABSTRACT

'UF15-6-28' is a new *Coleus* plant with novel characteristics that include excellent heat tolerance, distinct, lance-shaped leaves that display a unique and consistent crimson and chartreuse coloration pattern, and a vigorous, compact mounded growth habit with excellent lateral branching. 'UF15-6-28' exhibits superior foliage color stability when grown under all conditions, including both sun and shade conditions. Further, 'UF15-6-28' exhibits long-season performance until late fall.

3 Drawing Sheets

Latin name of the genus and species of the plant claimed: *Plectranthus scutellarioides.*

Cultivar denomination: 'UF15-6-28'.

BACKGROUND OF THE INVENTION

The invention relates to a new and distinct cultivar of *Coleus* plant that has been designated 'UF15-6-28'. This cultivar originated from an open pollination between the female *Coleus* plant 'UF13-45-3' (unpatented) and an unknown male *Coleus* plant. This open pollination was conducted in Gainesville, Fla. from May through November of 2014. Asexual propagation of 'UF15-6-28' first occurred in Gainesville, Fla. in May of 2015 using meristem tip cuttings. That and all subsequent asexual propagations of 'UF15-6-28' have remained true-to-type and retained the distinctive features of this novel cultivar.

SUMMARY OF THE INVENTION

The following are the most outstanding and distinguishing characteristics of 'UF15-6-28' when grown in Gainesville, Fla. under typical horticultural practices. 'UF15-6-28' exhibits excellent heat tolerance and distinct, lance-shaped leaves that display a unique and consistent crimson and chartreuse coloration pattern. Also, 'UF15-6-28' exhibits superior foliage color stability when grown under all conditions, including both sun and shade conditions. In particular, leaf coloration patterns like that exhibited by 'UF15-6-28' will fade in full sun to the point that the leaves become uniformly red at the expense of any chartreuse coloration; however, 'UF15-6-28' is unique in that well-defined zones of crimson and chartreuse coloration are retained in both shade and full sun. 'UF15-6-28' also exhibits a vigorous, compact mounded growth habit and excellent lateral branching, and thus provides ample vegetative propagules for producers when utilized as a stock plant. Further, 'UF15-6-28' exhibited long-season performance until late fall in landscape trials that were performed in Gainesville, Fla.

'UF15-6-28' can be distinguished from its female parent, 'UF13-45-3', at least based upon leaf shape, leaf coloration pattern, and plant growth habit. 'UF15-6-28' exhibits large lance-shaped leaves that are distinctly longer and less wide than those of 'UF13-45-3'. The leaves of 'UF15-6-28' are characterized by crimson centers and pronounced, irregular chartreuse margins; whereas, those of 'UF13-45-3' are predominantly dark red. 'UF15-6-28' exhibits a robust, well-branched mounded habit; whereas, that of 'UF13-45-3' is vigorous but distinctly more upright and with less lateral branching.

'UF12-82-3' (U.S. Plant Pat. No. 27,288), and 'UF12-73-5' (U.S. Plant Pat. No. 27,499), exhibit lance-shaped leaves and a mounded habit similar to that of 'UF15-6-28'. However, neither 'UF12-82-3' or 'UF12-73-5' exhibit the foliage color pattern displayed by 'UF15-6-28'.

BRIEF DESCRIPTION OF THE DRAWINGS

This new *Coleus* plant is illustrated by the accompanying photographs, which show the plant's form and foliage. The colors shown are as true as can be reasonably obtained by conventional photographic procedures. The photographs in FIGS. 2 and 3 are of plants that were grown from unrooted cuttings in a poly-covered plastic greenhouse in Gainesville, Fla. for 11 weeks from November, 2017 through February, 2018.

DETAILED BOTANICAL DESCRIPTION

Figure 1:
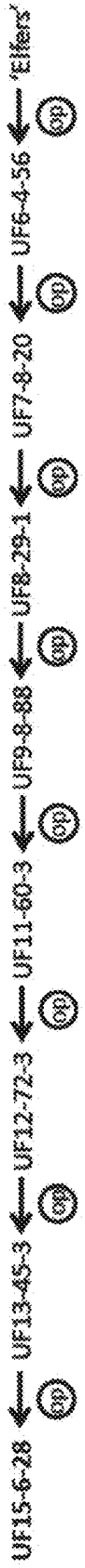
FIG. 1—Shows the pedigree of 'UF15-6-28'.
Figure 2:
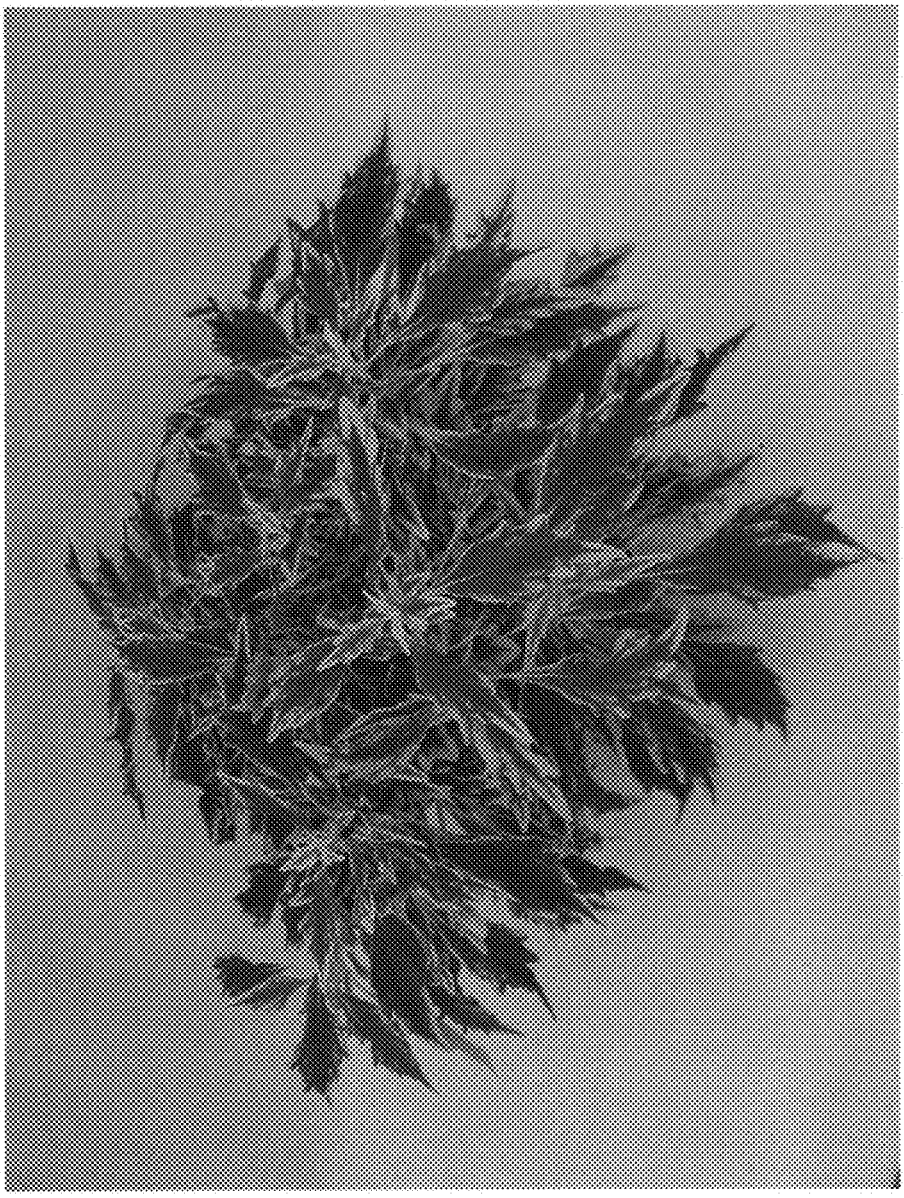
FIG. 2—Shows the growth habit, form, and foliage of 'UF15-6-28'.
Figure 3:
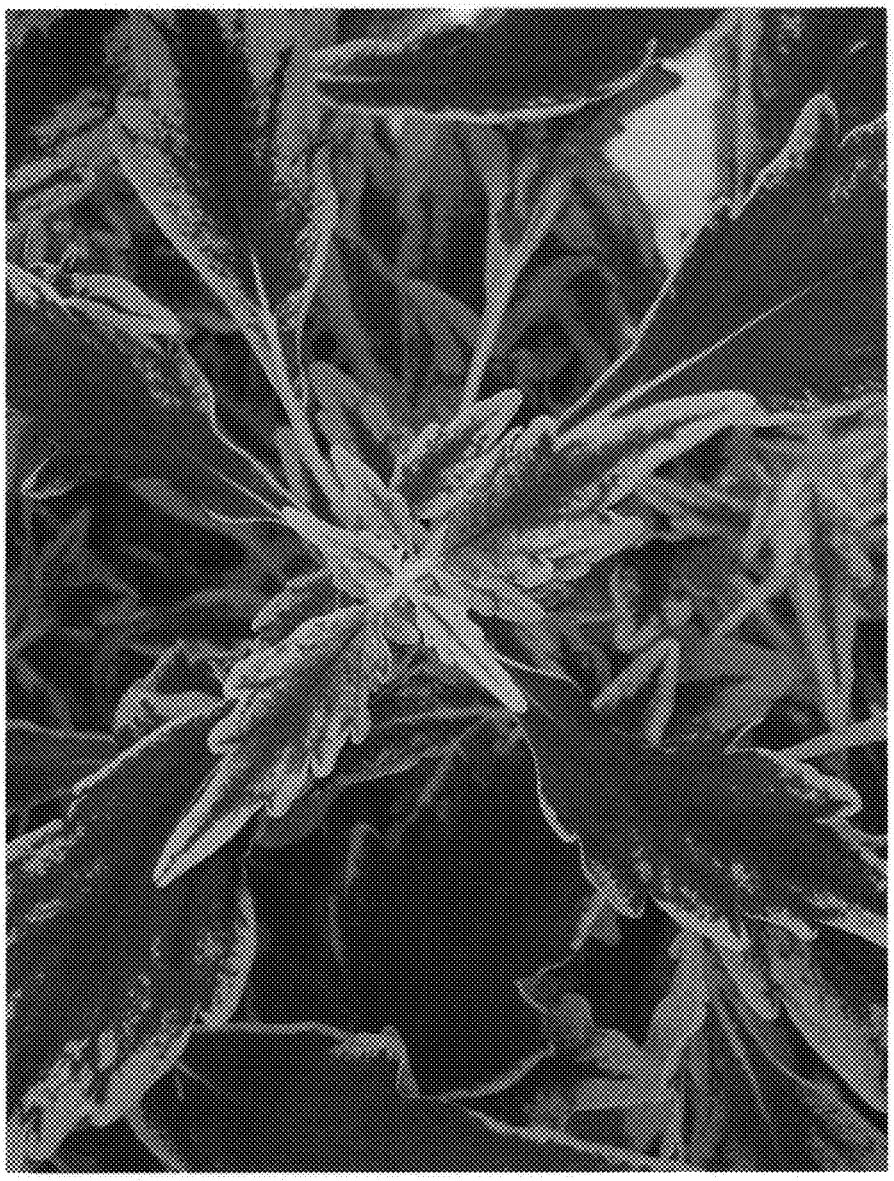
FIG. 3—Shows a close-up of the foliage of 'UF15-6-28'.

The following detailed description sets forth the distinctive characteristics of 'UF15-6-28'. The detailed description was obtained using 10-week-old plants grown from unrooted cuttings during November, 2017 through February, 2018 in a poly-covered plastic greenhouse in Gainesville, Florida. The plants were propagated in mist for 10 days after cuttings were stuck, and then they were grown in 1-gallon pots for approximately 9 weeks. Color references are to The R.H.S. Colour Chart of The Royal Horticultural Society of London (R.H.S.), 2007 5th Edition.

Classification:

*Family.*—*Lamiaceae.*

*Botanical.*—*Plectranthus scutellarioides.*

*Common name.*—*Coleus.*

*Cultivar name.*—'UF15-6-28'.

Plant description:

*Form.*—Spreading.

*Habit.*—Mounded.

*Height* (*from top of soil*).—15-20 cm.

*Width* (*horizontal plant diameter*).—45-50 cm.

Propagation:

*Type cuttings.*—Vegetative meristems having at least 1 node.

*Time to initiate roots.*—3-4 days.

*Time to produce a rooted cutting.*—7-10 days.

*Root habit.*—Fibrous.

*Root description.*—Callus forms in 2-3 days; roots initiate in 3-4 days; and roots become highly branched in 7-10 days.

Branches:

*Quantity per plant.*—8.

*Branch color.*—Yellow green, RHS 145A.

*Texture.*—Smooth.

*Pubescence.*—Not present.

*Stem description.*—Square-shaped and 0.7 cm in diameter at the soil line.

*Branch diameter.*—0.4-0.5 cm at the base of a 16 cm long branch.

*Branch length.*—14-16 cm.

*Internode length.*—2.0-2.5 cm.

*Anthocyanin.*—Yellow green, RHS 145A.

Leaves:

*Quantity of leaves per branch.*—16-20. Arrangement: Opposite.

*Fragrance.*—Not fragrant.

*Shape.*—Elliptic.

*Length.*—10-12 cm.

*Width.*—4-5 cm.

*Apex.*—Narrowly acute.

*Base.*—Attenuate.

*Margin.*—Lobed.

*Leaf texture* (*both surfaces*).—Smooth.

*Pubescence color* (*both surfaces*).—Not present.

*Venation color.*—Upper surface: Center=Purplish red, RHS N79A; Edges=Red, RHS 187B. Lower surface: Yellow green, RHS 145C.

*Venation pattern.*—Upper surface: Arcuate. Lower surface: Reticulate.

*Color.*—Immature leaf: Upper surface: Center=Red, RHS 187C; Margin=Yellow, RHS N144B. Lower surface: Center=Red, RHS 187B; Margin=Yellow green, RHS N150C.

*Color.*—Mature leaf: Upper surface: Center=Red, RHS 187B; Margin=Yellow green, RHS N144C. Lower surface: Center=Yellow green, RHS 146D; Margin=Yellow green, RHS N144C.

*Petiole length.*—4.0-4.5 cm.

*Petiole diameter.*—0.1-0.2 cm.

*Petiole color.*—Yellow green, RHS 145B.

*Petiole texture.*—Smooth, no pubescence.

Flowers and seeds: Not observed.

Fruit/seed set: Not observed.

Disease and insect resistance: The disease and insect resistance of this cultivar is typical of its species. The most common insect pests observed on this plant in Gainesville, Fla. have been long-tailed or citrus mealybugs (*Pseudococcus* sp.), which occurred on older stock plant material that had been held in the greenhouse for over 3-4 months. *Impatiens* Necrotic Spot Virus (*Bunyaviridae*) has also been observed in plants that were confined in greenhouses with mixed crops (peppers) that were infected with Western flower thrips (*Frankliniella occidentalis*). The most common pathogen of this species in the U.S. is downy mildew (*Peronospora lamii*) and it has been observed in stock materials grown closely together during the cooler growing seasons.

What is claimed is:

1. A new and distinct *Plectranthus scutellarioides* plant called 'UF15-6-28' as shown and described herein.

* * * * *